(12) United States Patent
Lee et al.

(10) Patent No.: US 11,476,025 B2
(45) Date of Patent: *Oct. 18, 2022

(54) MRI-COMPATIBLE MAGNET APPARATUS

(71) Applicant: ADVANCED BIONICS AG, Staefa (CH)

(72) Inventors: Sung Jin Lee, Valencia, CA (US); Jeryle L. Walter, Valencia, CA (US); James George Elcoate Smith, Valencia, CA (US); Uli Gommel, Valencia, CA (US); Stephanie M. Reed, Conshohocken, PA (US)

(73) Assignee: Advanced Bionics AG, Staefa (CH)

( * ) Notice: Subject to any disclaimer, the term of this patent is extended or adjusted under 35 U.S.C. 154(b) by 32 days.

This patent is subject to a terminal disclaimer.

(21) Appl. No.: 17/008,291

(22) Filed: Aug. 31, 2020

(65) Prior Publication Data
US 2020/0391023 A1    Dec. 17, 2020

Related U.S. Application Data

(63) Continuation of application No. 16/009,600, filed on Jun. 15, 2018, now Pat. No. 10,821,279, which is a
(Continued)

(51) Int. Cl.
*H01F 7/02*     (2006.01)
*A61N 1/375*   (2006.01)
(Continued)

(52) U.S. Cl.
CPC ......... *H01F 7/0205* (2013.01); *A61N 1/3758* (2013.01); *A61N 1/0541* (2013.01); *A61N 1/36038* (2017.08); *A61N 1/37229* (2013.01)

(58) Field of Classification Search
CPC ... H01F 7/0205; A61N 1/3758; A61N 1/0541; A61N 1/36038; A61N 1/37229; A61N 1/08; A61N 1/36036
See application file for complete search history.

(56) References Cited

U.S. PATENT DOCUMENTS 4,214,366 A    7/1980  Laban
4,352,960 A   10/1982  Dormer et al.
(Continued)

FOREIGN PATENT DOCUMENTS

DE    202006017662 U1    9/2007
EP          0241307 A2    10/1987
(Continued)

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
(Continued)

*Primary Examiner* — Catherine M Voorhees
(74) *Attorney, Agent, or Firm* — Henricks Slavin LLP

(57) ABSTRACT

A cochlear implant including a cochlear lead, an antenna, a stimulation processor, and a magnet apparatus, associated with the antenna, including a case defining a central axis, a magnet frame within the case and rotatable about the central axis of the case, and a plurality of elongate diametrically magnetized magnets that are located in the magnet frame, the magnets defining a longitudinal axis and a N-S direction and being freely rotatable about the longitudinal axis relative to the magnet frame.

23 Claims, 12 Drawing Sheets

Related U.S. Application Data continuation-in-part of application No. PCT/US2016/056351, filed on Oct. 11, 2016, which is a continuation-in-part of application No. PCT/US2015/066862, filed on Dec. 18, 2015.

(51) Int. Cl.
  *A61N 1/372* (2006.01)
  *A61N 1/36* (2006.01)
  *A61N 1/05* (2006.01)

(56) References Cited

U.S. PATENT DOCUMENTS

| | | |
|---|---|---|
| 4,595,390 A | 6/1986 | Hakim et al. |
| 4,606,329 A | 8/1986 | Hough |
| 4,612,915 A | 9/1986 | Hough et al. |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |
| 6,032,677 A | 3/2000 | Blechman et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,461,288 B1 | 10/2002 | Holcomb |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,266,208 B2 | 9/2007 | Charvin et al. |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,027,735 B1 | 9/2011 | Tziviskos et al. |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 * | 3/2018 | Lee .................. H01F 7/0205 |
| 9,931,501 B2 | 4/2018 | Smyth |
| 10,300,276 B2 | 5/2019 | Lee et al. |
| 10,463,849 B2 * | 11/2019 | Lee .................. A61N 1/3758 |
| 10,532,209 B2 * | 1/2020 | Lee .................. H04R 25/606 |
| 10,646,712 B2 | 5/2020 | Smith et al. |
| 10,646,718 B2 | 5/2020 | Smith et al. |
| 10,806,936 B2 | 10/2020 | Crawford et al. |
| 10,821,279 B2 * | 11/2020 | Lee .................. H01F 7/0205 |
| 11,097,095 B2 | 8/2021 | Smith et al. |
| 11,287,495 B2 | 3/2022 | Smith et al. |
| 11,364,384 B2 | 6/2022 | Smith et al. |
| 2004/0012470 A1 | 1/2004 | Zimmerling et al. |
| 2004/0059423 A1 | 3/2004 | Barnes et al. |
| 2004/0063072 A1 | 4/2004 | Honkura et al. |
| 2004/0210103 A1 | 10/2004 | Westerkull |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0015155 A1 | 1/2006 | Charvin et al. |
| 2006/0116743 A1 | 6/2006 | Gibson et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0097496 A1 | 4/2008 | Chang et al. |
| 2008/0103350 A1 | 5/2008 | Farone |
| 2008/0192968 A1 | 8/2008 | Ho et al. |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 * | 9/2011 | Zimmerling .......... H04L 12/1877 607/57 |
| 2011/0255731 A1 | 10/2011 | Ball |
| 2011/0264172 A1 * | 10/2011 | Zimmerling .......... A61N 1/36038 607/60 |
| 2012/0296155 A1 | 11/2012 | Ball |
| 2013/0079749 A1 | 3/2013 | Overstreet et al. |
| 2013/0150657 A1 | 6/2013 | Leigh et al. |
| 2013/0184804 A1 | 7/2013 | Dalton |
| 2013/0281764 A1 | 10/2013 | Bjorn et al. |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0336447 A1 | 11/2014 | Bjorn et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0094521 A1 | 4/2015 | Neuman et al. |
| 2015/0100109 A1 | 4/2015 | Feldman et al. |
| 2015/0112407 A1 | 4/2015 | Hartley et al. |
| 2015/0265842 A1 | 9/2015 | Ridker |
| 2015/0320523 A1 | 11/2015 | Way et al. |
| 2015/0367126 A1 | 12/2015 | Smyth |
| 2015/0382114 A1 | 12/2015 | Andersson et al. |
| 2016/0008596 A1 | 1/2016 | Gibson et al. |
| 2016/0023006 A1 | 1/2016 | Ridler et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0213936 A1 | 7/2016 | Heerlein et al. |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |

(56) References Cited

U.S. PATENT DOCUMENTS

| | | |
|---|---|---|
| 2017/0078808 A1 | 3/2017 | Kennes |
| 2017/0156010 A1 | 6/2017 | Verma et al. |
| 2017/0239476 A1 | 8/2017 | Lee et al. |
| 2017/0347208 A1 | 11/2017 | Jurkiewicz |
| 2018/0028818 A1 | 2/2018 | Andersson et al. |
| 2018/0056084 A1 | 3/2018 | Alam |
| 2018/0110985 A1 | 4/2018 | Walter |
| 2018/0110986 A1 | 4/2018 | Lee |
| 2018/0133486 A1 | 5/2018 | Smith |
| 2018/0146308 A1 | 5/2018 | Leigh et al. |
| 2018/0160241 A1 | 6/2018 | Gustafsson et al. |
| 2018/0160242 A1 | 6/2018 | Sriskandarajah |
| 2018/0185634 A1 | 7/2018 | Smyth |
| 2018/0249262 A1 | 8/2018 | Santek |
| 2018/0270591 A1 | 9/2018 | Kennes |
| 2018/0296826 A1 | 10/2018 | Lee et al. |
| 2018/0303602 A1 | 10/2018 | Leigh |
| 2018/0304078 A1 | 10/2018 | Crawford et al. |
| 2018/0369586 A1 | 12/2018 | Lee et al. |
| 2019/0015662 A1 | 1/2019 | Raje et al. |
| 2019/0046797 A1 | 2/2019 | Calixto et al. |
| 2019/0053908 A1 | 2/2019 | Cook et al. |
| 2019/0076649 A1 | 3/2019 | Lee et al. |
| 2019/0255316 A1 | 8/2019 | Lee et al. |
| 2019/0298417 A1 | 10/2019 | Barrett et al. |
| 2020/0114151 A1 | 4/2020 | Smith et al. |
| 2020/0230422 A1 | 7/2020 | Gibson et al. |
| 2020/0330777 A1 | 10/2020 | Smith et al. |
| 2021/0046311 A1 | 2/2021 | Brehm et al. |
| 2021/0106815 A1 | 4/2021 | Smith et al. |
| 2021/0156934 A1 | 5/2021 | Smith et al. |
| 2021/0299456 A1 | 9/2021 | Smith et al. |
| 2021/0316136 A1 | 10/2021 | Smith et al. |
| 2021/0339021 A1 | 11/2021 | Brehm et al. |

FOREIGN PATENT DOCUMENTS

| | | |
|---|---|---|
| EP | 2117489 B1 | 5/2010 |
| EP | 2853287 A1 | 4/2015 |
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004004416 A1 | 1/2004 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2012010195 A1 | 1/2012 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |
| WO | WO2018200347 A1 | 11/2018 |
| WO | WO2018217187 A1 | 11/2018 |
| WO | WO2019027745 A1 | 2/2019 |
| WO | WO2019083540 A1 | 5/2019 |
| WO | WO2019160555 A1 | 8/2019 |
| WO | WO2020092185 A1 | 5/2020 |
| WO | WO2021201845 A1 | 10/2021 |

OTHER PUBLICATIONS

Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.
PCT International Search and Written Opinion dated Mar. 14, 2016 for PCT App. Ser. No. PCT/US2015/066862.
PCT International Search and Written Opinion dated Jan. 4, 2017 for PCT App. Ser. No. PCT/US2016/056351.
U.S. Appl. No. 15/568,469, filed Oct. 21, 2017, 20180110985 A1.
U.S. Appl. No. 15/770,207, filed Apr. 22, 2018, now U.S. Pat. No. 10,806,936.
U.S. Appl. No. 17/073,322, filed Oct. 17, 2020, 20210170167 A1.
U.S. Appl. No. 16/060,383, filed Jun. 7, 2018, now U.S. Pat. No. 10,532,209.
U.S. Appl. No. 15/591,054, filed May 9, 2017, now U.S. Pat. No. 9,919,154.
U.S. Appl. No. 16/009,600, filed Jun. 15, 2018, now U.S. Pat. No. 10,821,279.
U.S. Appl. No. 16/403,582, filed May 5, 2019, now U.S. Pat. No. 10,463,849.
U.S. Appl. No. 17/008,291, filed Aug. 31, 2010, 20200391023 A1.
U.S. Appl. No. 16/610,502, filed Nov. 2, 2019, now U.S. Pat. No. 11,287,495.
U.S. Appl. No. 15/568,470, filed Oct. 21, 2017, now U.S. Pat. No. 10,300,276.
U.S. Appl. No. 16/101,390, filed Aug. 10, 2018, 20190046797 A1.
U.S. Appl. No. 15/703,808, filed Sep. 13, 2017, now U.S. Pat. No. 10,646,712.
U.S. Appl. No. 15/805,025, filed Nov. 6, 2017, now U.S. Pat. No. 10,646,718.
U.S. Appl. No. 16/852,457, filed Apr 18, 2020, 20200238088 A1.
U.S. Appl. No. 16/499,311, filed Sep. 29, 2019, now U.S. Pat. No. 11,097,095.
U.S. Appl. No. 17/355,225, filed Jun. 23, 2021, 20210316136 A1.
U.S. Appl. No. 16/603,868, filed Oct. 9, 2019, now U.S. Pat. No. 11,364,384.
U.S. Appl. No. 16/754,126, filed Apr. 6, 2020, 20200330777 A1.
U.S. Appl. No. 17/335,161, filed Jun. 1, 2021, 20210339021 A1.
U.S. Appl. No. 17/346,343, filed Jun. 14, 2021, 20210299456 A1.
U.S. Appl. No. 17/499,813, filed Oct. 12, 2021.

* cited by examiner

FIG. 2 - Prior Art

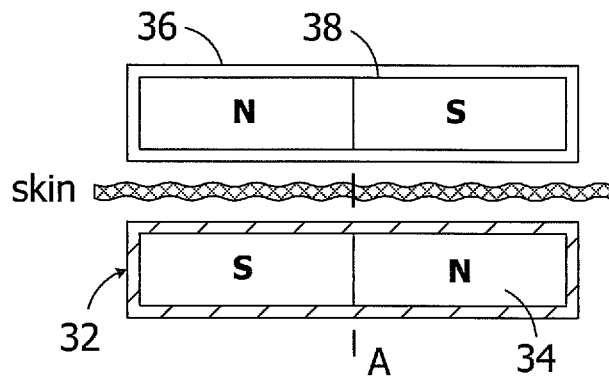
FIG. 5 - Prior Art
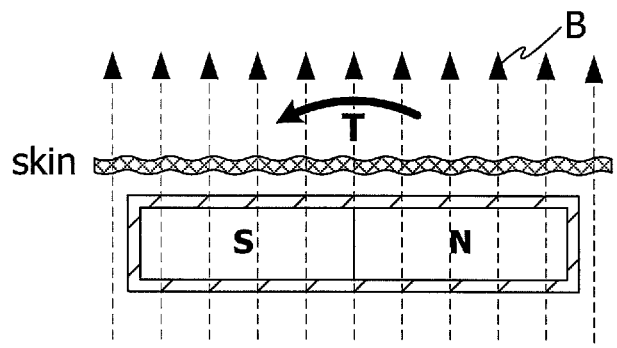
FIG. 6 - Prior Art
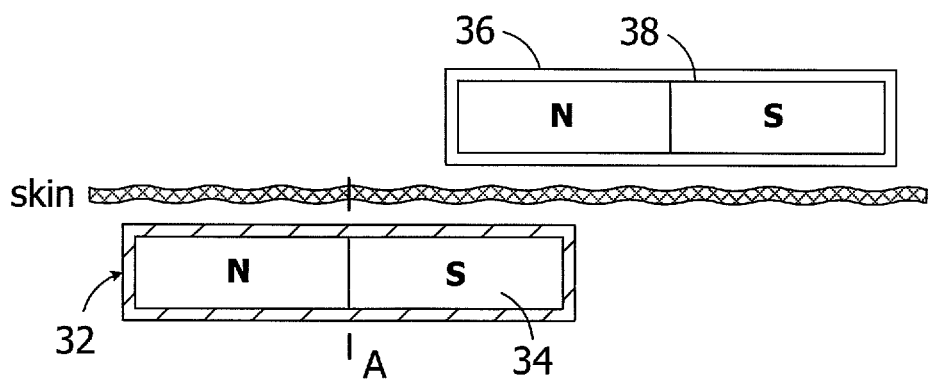
FIG. 6A - Prior Art

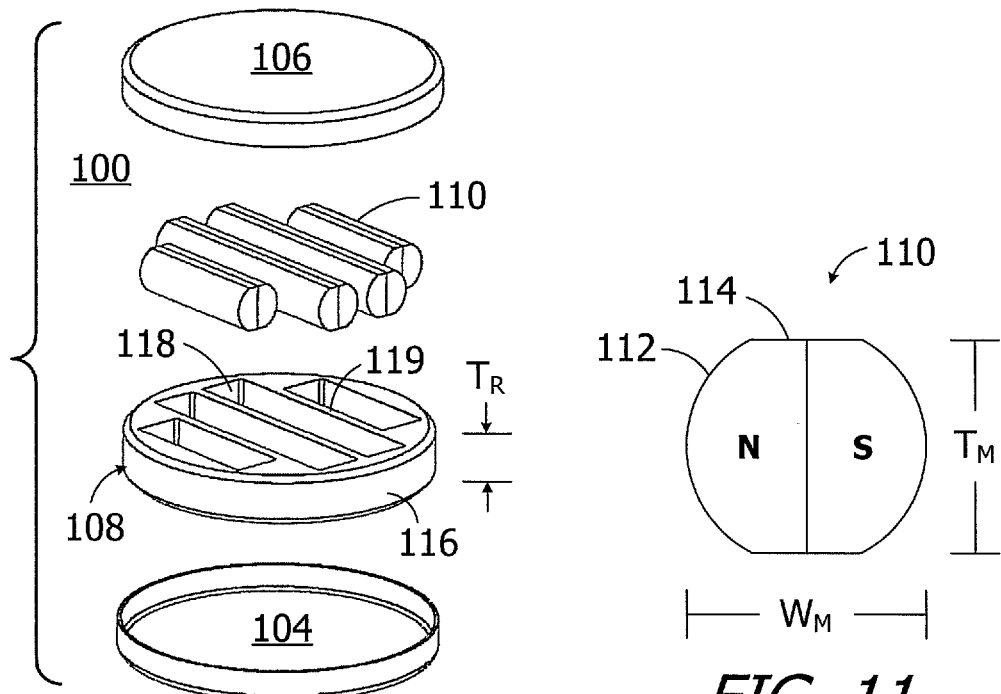
FIG. 10
FIG. 11
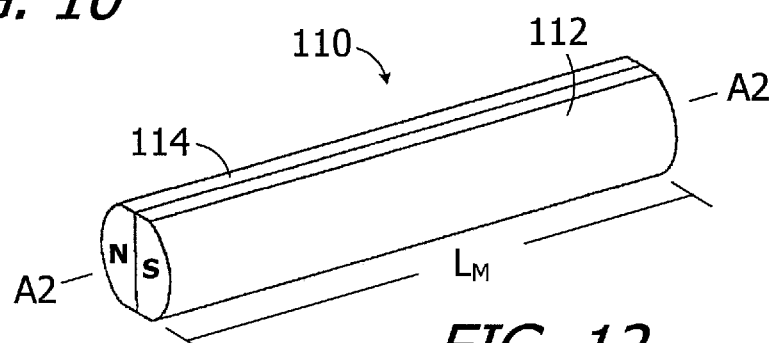
FIG. 12
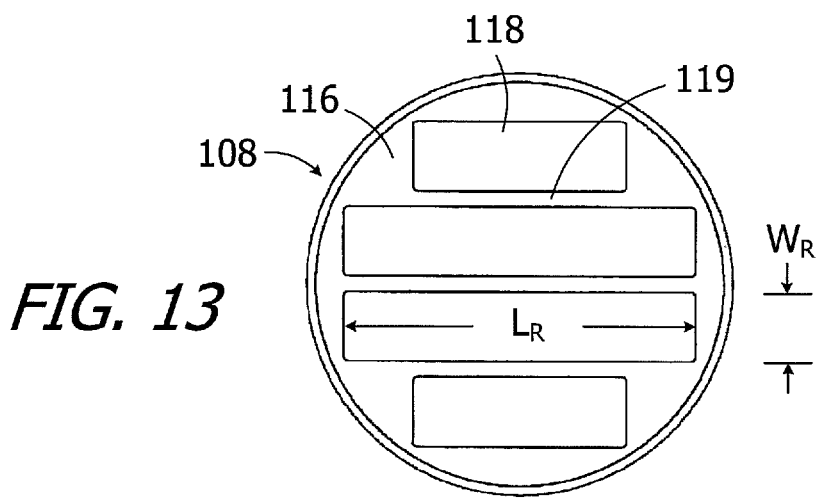
FIG. 13

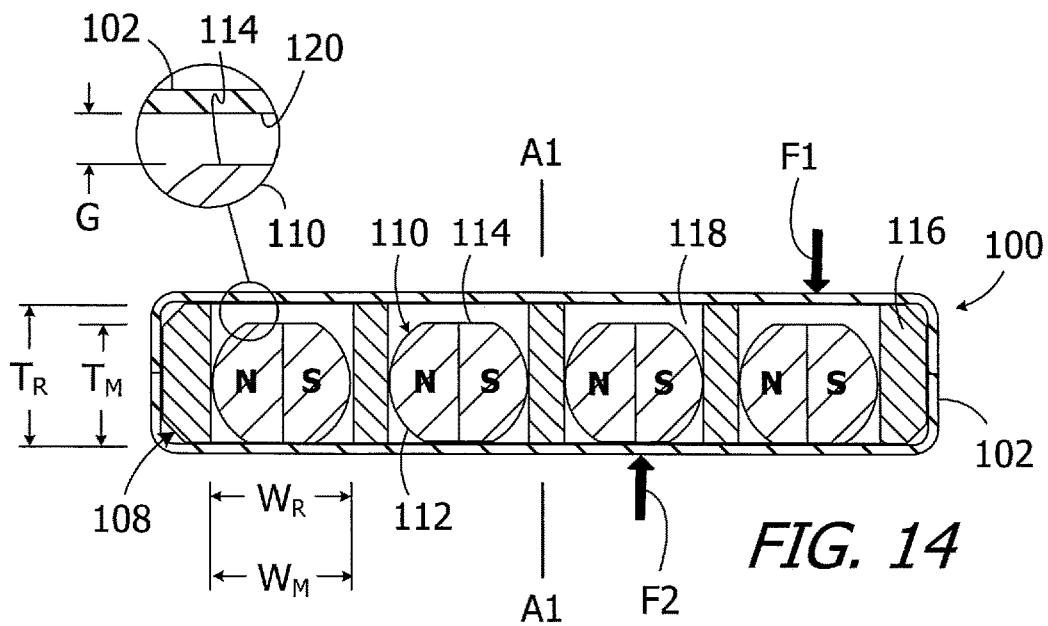
FIG. 14
FIG. 14A
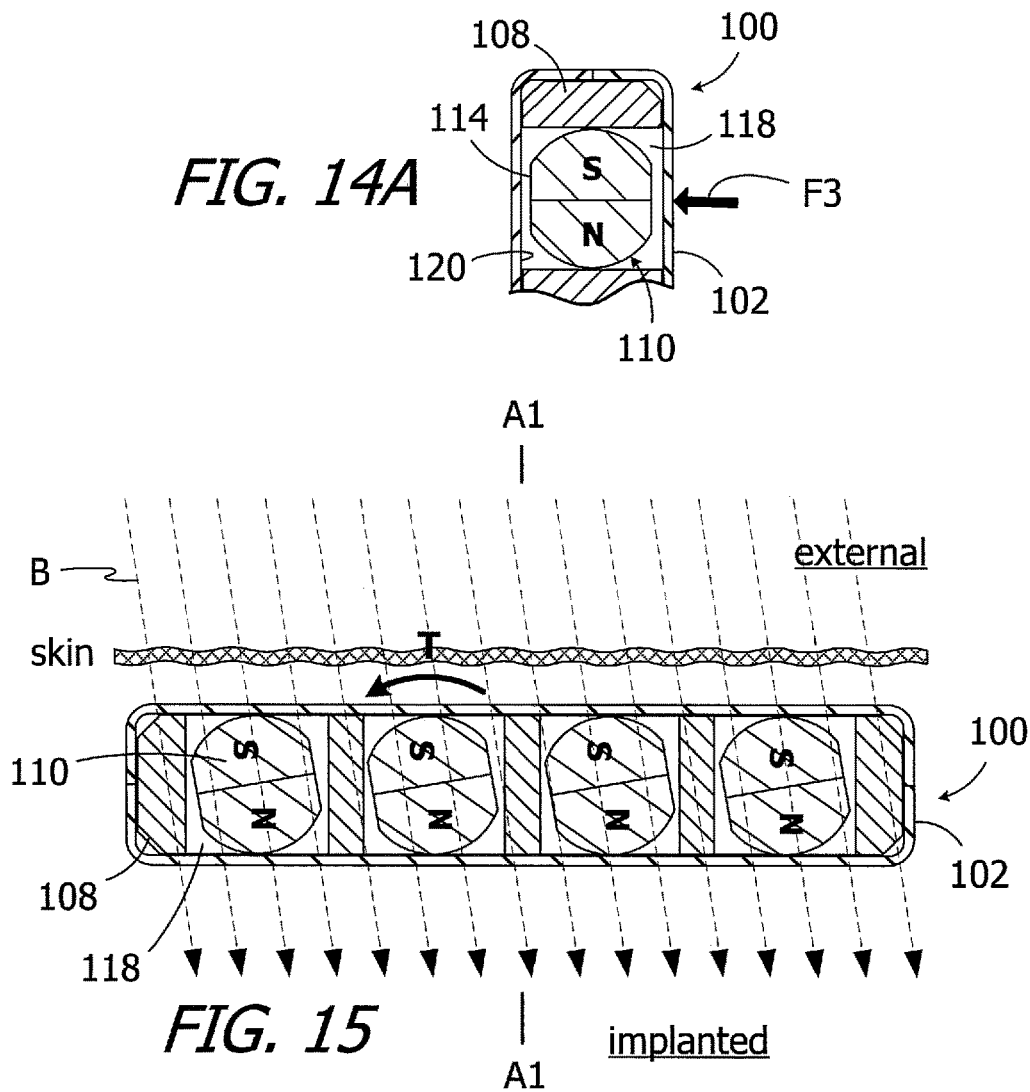
FIG. 15

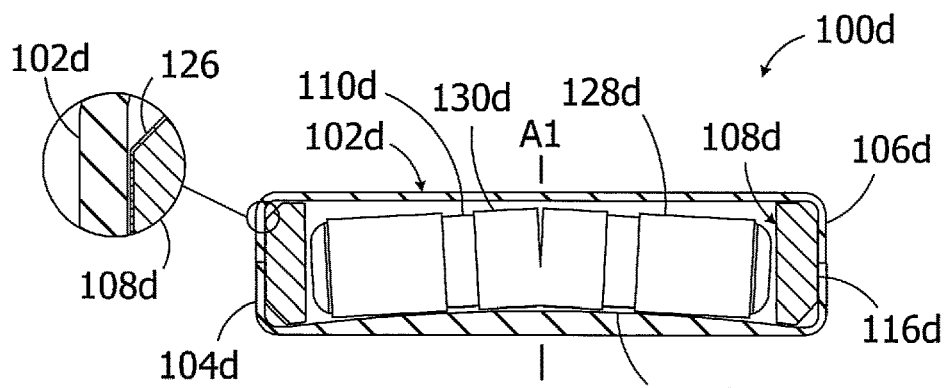
FIG. 35
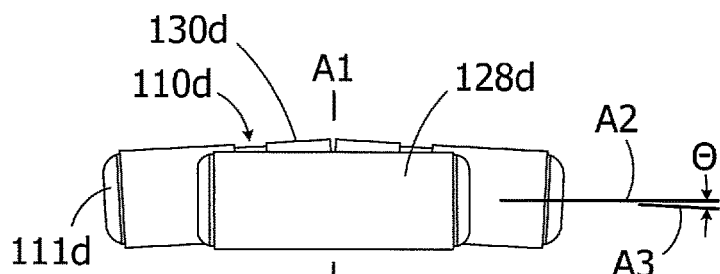
FIG. 36
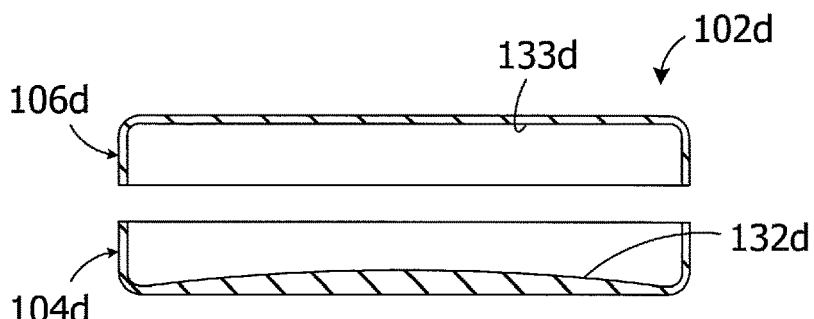
FIG. 37
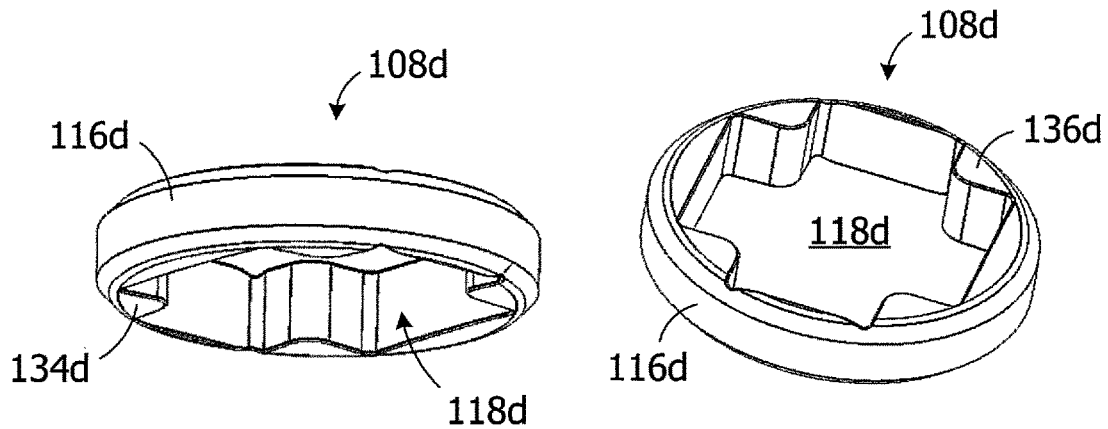
FIG. 38
FIG. 39

US 11,476,025 B2

MRI-COMPATIBLE MAGNET APPARATUS

CROSS-REFERENCE TO RELATED APPLICATIONS

This application is a continuation of U.S. application Ser. No. 16/009,600, filed Jun. 15, 2018, now U.S. Pat. No. 10,821,279, which is a continuation-in-part of, and claims priority to, International Application No. PCT/US2016/056351, filed Oct. 11, 2016, which is a continuation-in-part of, and claims priority to, International Application No. PCT/US2015/066862, filed Dec. 18, 2015, both of which are incorporated herein by reference in their entirety.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics Harmony™ BTE sound processor, the Advanced Bionics Naida CI Q Series BTE sound processors and the Advanced Bionics Neptune™ body worn sound processor.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 10 mm thick.

The magnitude of the retention force between the headpiece magnet and implant magnet is an important aspect of an ICS system. If the force is too low, the headpiece will not remain in place on the head during typical activities. If, on the other hand, the force is too high, the pressure on the skin flap can result is discomfort and tissue necrosis. The magnitude of the retention force is dictated by the strength of the magnets and the distance between the magnets, which is a function of the thickness of the skin flap. The strength of the headpiece magnet is frequently selected during the post-implantation headpiece fitting processes.

The present inventors have determined that conventional cochlear implants are susceptible to improvement. For example, the magnets in many conventional cochlear implants are disk-shaped and have north and south magnetic dipoles that are aligned in the axial direction of the disk. Such magnets are not compatible with magnetic resonance imaging ("MRI") systems. In particular, the cochlear implant 10 illustrated in FIG. 1 includes, among other things, a housing 12 and a disk-shaped solid block magnet 14. The implant magnet produces a magnetic field M in a direction that is perpendicular to the patient's skin and parallel to the axis A, and this magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may demagnetize the implant magnet 14 or generate a significant amount of torque T on the implant magnet 14. The torque T may dislodge the implant magnet 14 from the pocket within the housing 12, reverse the magnet 14 and/or dislocate the cochlear implant 10, all of which may also induce tissue damage. One proposed solution involves surgically removing the implant magnet 14 prior to the MRI procedure and then surgically replacing the implant magnet thereafter.

One proposed solution involves the use of freely rotatable ball magnets that create a magnetic field which can rotate, from the aforementioned direction that is perpendicular to the patient's skin, to a direction that is aligned with the direction of the MRI magnetic field B. To that end, and referring to FIG. 2, one proposed implantable magnet apparatus 20 includes a plurality of freely rotatable ball magnets 22 within a case 24. When the magnet apparatus 20 is in very close proximity to an external magnet 26, the ball magnets 22 will align with the external magnet 26 in the manner shown, with the N-S direction of the ball magnets being the same as that of the external magnet. When the external magnet 26 is removed (FIG. 3), the ball magnets 22 will align with one another. The ball magnets 22 will then rotate as necessary in response to the application of the MRI magnetic field, thereby minimizing the torque T, because the MRI magnetic field is far stronger than the attraction between the ball magnets. Turning to FIG. 4, the present inventors have determined that the use of freely rotatable ball magnets 22 is less than optimal because the distance between implanted ball magnets (located within a cochlear implant 28) and the external magnet 26 (located within an external headpiece 30) is so great that the magnetic attraction between the ball magnets is greater than the magnetic attraction between the ball magnets and the external magnet. The N-S direction of the ball magnets 22 is perpendicular to the N-S direction of the external magnet 26. The increased distance, as compared to the distance illustrated in FIG. 3, is a product of, for example, the presence of the implant and headpiece housings and the thickness of the skin flap. The weak magnetic attraction resulting from the misalignment of the magnetic fields prevents the headpiece from properly mounting to the patient's head. One possible solution is to simply increase the size of the external magnet, thereby increasing the strength of the associated magnetic field to the point at which the ball magnets 22 in a cochlear implant will rotate into the orientation illustrated in FIG. 2. The present inventors have determined, however, that the associated increase in the size and weight of the headpiece is undesirable.

Another proposed solution is illustrated in FIG. 5. Here, the cochlear implant 32 includes a diametrically magnetized disk-shaped magnet 34 that is rotatable relative to the remainder of the implant about an axis A, and that has a N-S orientation which is perpendicular to the axis A. The external headpiece 36 includes a diametrically magnetized disk-shaped magnet 38 that is not rotatable relative to the remainder of the headpiece. The implanted magnet 34 is able to rotate about the axis A into alignment with the external magnet 38, and is also able to rotate about the axis A into alignment with an MRI magnetic that is perpendicular to the axis A. Turning to FIG. 6, the present inventors have determined that the use of the diametrically magnetized disk-shaped magnet 34 is less than optimal because a dominant magnetic field (e.g., the MRI magnetic field B) that is misaligned by 30° or more may demagnetize the magnet or generate an amount of torque T on the magnet that is sufficient to dislodge or reverse the magnet and/or dislocate the associated cochlear implant.

Another issue is associated with those instances where the user does not precisely position the headpiece 38 over the cochlear implant 32. Referring to FIG. 5, when the headpiece 36 is precisely positioned over the cochlear implant 32, the diametrically magnetized implant magnet 34 will simply rotate into alignment with the non-rotatable diametrically magnetized headpiece magnet 38. The magnetic retention force will correspond to that selected during the fitting process. In those instances where the headpiece 36 is not precisely placed over the implant 32, and the implant magnet 34 will rotate into the magnetic alignment as shown in FIG. 6A. The magnetic retention force will not, however, be strong enough to pull the headpiece 36 (and its antenna) into alignment over the implant 32 (and its antenna). Moreover, even if the headpiece 36 eventually moves to the aligned position over the implant 32, the electronic lock between the sound processor unit and the cochlear implant will be based on the misaligned position.

SUMMARY

A cochlear implant in accordance with one of the present inventions may include a cochlear lead, an antenna, a stimulation processor, an implant magnet apparatus, associated with the antenna, including a case defining a central axis, a magnet frame within the case and rotatable about the central axis of the case, and a plurality of elongate diametrically magnetized magnets that are located in the magnet frame, the magnets defining a longitudinal axis and a N-S direction and being freely rotatable about the longitudinal axis relative to the magnet frame. A system in accordance with one of the present inventions includes such a cochlear implant and an external device. The external device may include an antenna and an external magnet.

There are a number of advantages associated with such apparatus and methods. For example, a strong magnetic field, such as an MRI magnetic field, will not demagnetize the magnet apparatus. Nor will it generate a significant amount of torque on the magnet apparatus and associated cochlear implant. As a result, surgical removal of the cochlear implant magnet prior to an MRI procedure, and then surgically replacement thereafter, is not required. Moreover, in the absence of the strong magnetic field, the magnetic attraction between rotatable magnets in the magnet apparatus will not cause the magnets to rotate into an undesirable N-S orientation.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 2 is a partial section view of a conventional implant magnet apparatus and external magnet.

FIG. 5 is a partial section view of a headpiece and an implanted cochlear implant with a conventional implant magnet apparatus.

FIG. 6 is a partial section view of the implanted cochlear implant with a conventional implant magnet apparatus illustrated in FIG. 5 in an MRI magnetic field.

FIG. 6A is a partial section view of the implanted cochlear implant and headpiece illustrated in FIG. 5 with the headpiece misaligned.

FIG. 10 is an exploded view of the implant magnet apparatus illustrated in FIG. 7.

FIG. 11 is an end view of a portion of the implant magnet apparatus illustrated in FIG. 7.

FIG. 12 is a perspective view of a portion of the implant magnet apparatus illustrated in FIG. 7.

FIG. 13 is a plan view of a portion of the implant magnet apparatus illustrated in FIG. 7.

FIG. 14 is a section view taken along line 14-14 in FIG. 7.

FIG. 14A is a section view showing a portion of the implant magnet apparatus illustrated in FIG. 14 in a different orientation.

FIG. 15 is a section view similar to FIG. 14 with the implant magnet apparatus in an MRI magnetic field.

FIG. 35 is a section view taken along line 35-35 in FIG. 30.

FIG. 36 is a side view of a portion of the implant magnet apparatus illustrated in FIG. 30.

FIG. 37 is an exploded section view of a portion of the implant magnet apparatus illustrated in FIG. 30.

FIG. 38 is a perspective view of a portion of the implant magnet apparatus illustrated in FIG. 30.

FIG. 39 is a perspective view of a portion of the implant magnet apparatus illustrated in FIG. 30.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
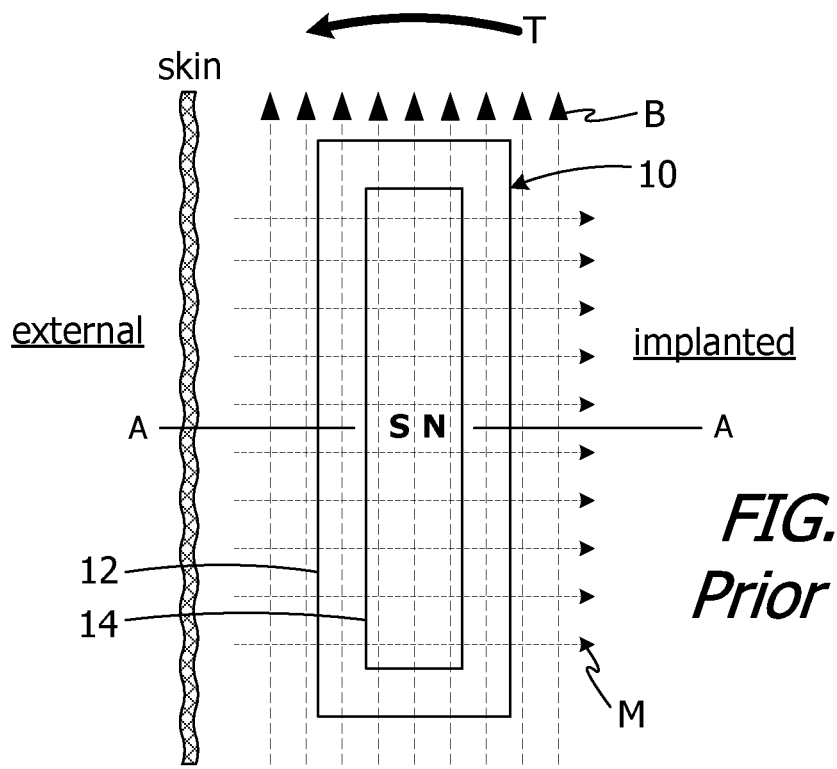
FIG. 1 is a plan view showing a conventional cochlear implant in an MRI magnetic field.
Figure 3:
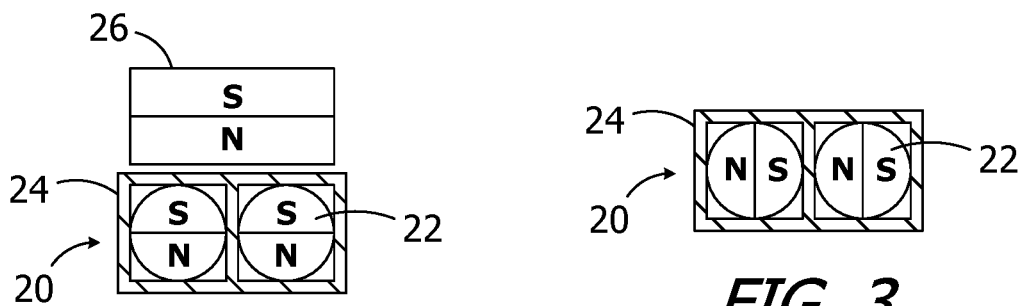
FIG. 3 is a partial section view of a conventional implant magnet apparatus.
Figure 4:
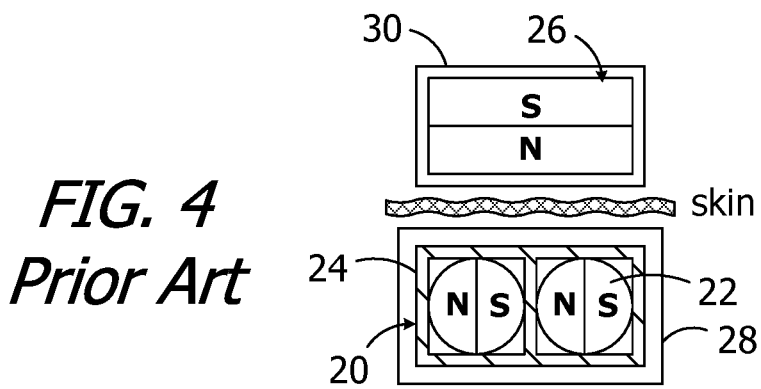
FIG. 4 is a partial section view of a headpiece and an implanted cochlear implant with a conventional implant magnet apparatus.
Figure 7:
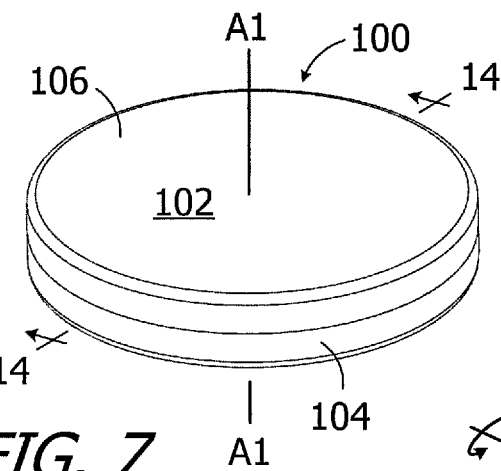
FIG. 7 is a perspective view of an implant magnet apparatus in accordance with one embodiment of a present invention.
Figure 8:
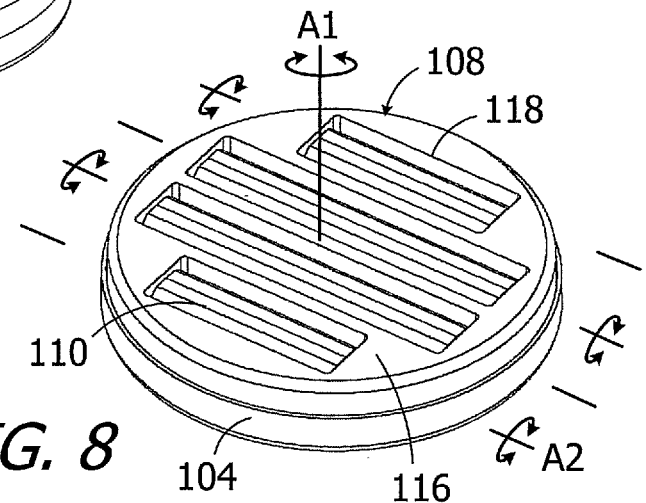
FIG. 8 is a perspective view of a portion of the implant magnet apparatus illustrated in FIG. 7.

As illustrated for example in FIGS. 7 and 8, an exemplary magnet apparatus 100 includes a case 102, with base 104 and a cover 106, a magnet frame 108, and a plurality of elongate diametrically magnetized magnets 110 within the frame that define a N-S direction. The magnet apparatus 100 may, in some instances, be employed a system 50 (FIG. 9) that includes a cochlear implant 200 (described below with reference to FIG. 46) with the magnet apparatus 100 and an external device such as a headpiece 400 (described below with reference to FIG. 47). The headpiece 400 includes, among other things, a housing 402 and a diametrically magnetized disk-shaped positioning magnet 410 that is not rotatable relative to the housing.

The exemplary case 102 is disk-shaped and defines a central axis A1, which is also the central axis of the magnet frame 108. The magnet frame 108 is freely rotatable relative to the case 102 about the central axis A1 over 360°. The magnets 110 rotate with the magnet frame 108 about the central axis A1. Each magnet 110 is also freely rotatable relative to the magnet frame 108 about its own longitudinal axis A2 (also referred to as "axis A2") over 360°. As used herein, the phrase "freely rotatable about an axis" refers to an object that can rotate about an axis relative to an adjacent object, albeit with some friction between the two object, without mechanical limitation of the rotation (e.g., with a stop or biasing device that opposes the rotation). In the illustrated implementation, the longitudinal axes A2 are parallel to one another and are perpendicular to the central axis A1. In other implementations, the magnets within a magnet apparatus may be oriented such that the longitudinal axes thereof are at least substantially perpendicular to the central axis A1. As used herein, an axis that is "at least substantially perpendicular to the central axis" includes axes that are perpendicular to the central axis as well as axes that are slightly non-perpendicular to the central axis (i.e., axes that are offset from perpendicular by up to 5 degrees). Examples of such magnet apparatus are described below with reference to FIGS. 30-45.

Figure 9:
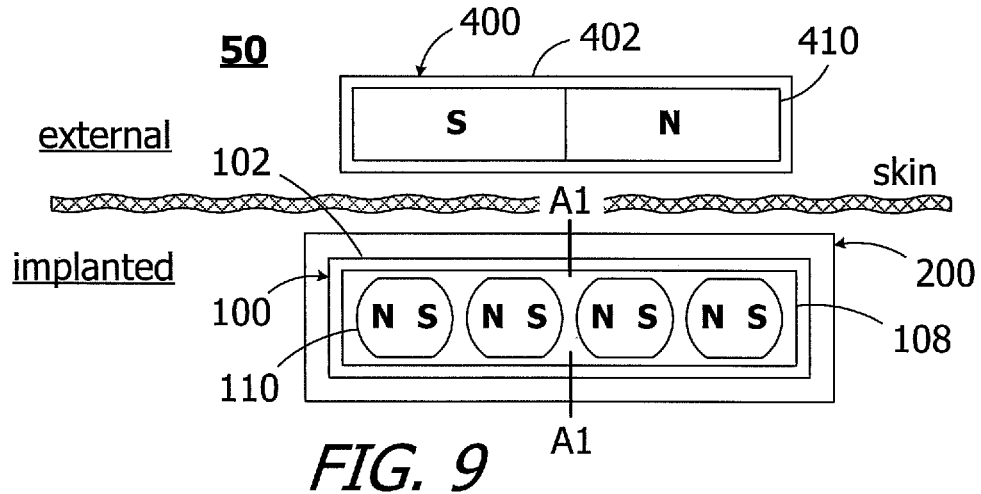
FIG. 9 is a diagrammatic view of a system including the magnet apparatus illustrated in FIG. 7 and a headpiece.

Given the ability of each magnet 110 to freely rotate about its longitudinal axis A2, the magnets 110 align with one another in the N-S direction in the absence of a relatively strong external magnetic field (e.g., the MRI magnetic field discussed above), and the at rest N-S orientation of the magnets 110 will be perpendicular to the central axis A1, as is illustrated in FIGS. 9 and 14. So oriented, the magnetic fields of the diametrically magnetized magnets 110 are aligned with the magnetic field of the diametrically magnetized disk-shaped positioning magnet 410.

Figure 9A:
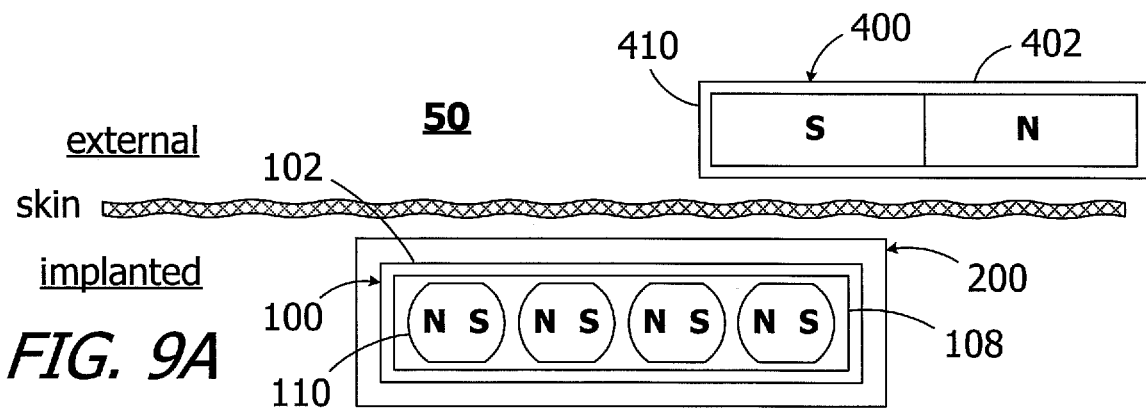
FIG. 9A is a diagrammatic view of a system including the magnet apparatus illustrated in FIG. 7 and a misaligned headpiece.

It should also be noted here that the magnetic field of the positioning magnet 410 is not strong enough to cause the magnets 110 to rotate out of the illustrated at rest N-S orientation. Although the frame 108 will rotate as necessary, the magnets 110 will remain in the N-S orientation illustrated in FIG. 9 and will continue to function as a magnetic unit in the presence of a headpiece magnet. As a result, when the associated headpiece is initially misaligned in the manner illustrated in FIG. 9A, the magnetic retention force will be strong enough to pull the headpiece 400 (and its antenna) into alignment over the implant 200 (and its antenna).

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 (as well as the cases 102b-102e described below with reference to FIGS. 21-45) may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultrahigh-molecular-weight polyethylene (UHMWPE), polytetrafluoroethylene (PTFE) and polyamide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 may have an overall size and shape similar to that of conventional cochlear implant magnets so that the magnet apparatus 100 can be substituted for a conventional magnet in an otherwise conventional cochlear implant. In some implementations, the diameter that may range from 9 mm to 16 mm and the thickness may range from 1.5 mm to 3.0 mm. The diameter of the case 102 is 12.9 mm, and the thickness is 2.4 mm, in the illustrated embodiment.

Although the present inventions are not limited to any particular number, there are four elongate diametrically magnetized magnets 110 in the exemplary magnet apparatus 100. Two of the otherwise identical magnets 110 are relatively long and two are relatively short in order to efficiently utilize the available volume within the case 102, as is best shown in FIG. 8. Turning to FIGS. 10-12, the exemplary magnets 110 are non-circular in a cross-section that is perpendicular to the longitudinal axis A2 and, in the illustrated implementation, include curved surfaces 112 and flat surfaces 114. The magnet width $W_M$, which extends in the N-S direction, is greater than the magnet thickness $T_M$, which extends in a direction perpendicular to the N-S direction. The use of elongate diametrically magnetized magnets that are larger in the N-S direction than in the direction perpendicular thereto reduces the likelihood of magnet damage, as is discussed in greater detail below with reference to FIG. 14. Nevertheless, in other implementations, the cross-sectional shape may be circular. The magnet lengths LM of the relatively long and short magnets 110, i.e. the length in the direction of longitudinal axis A2, are greater than the magnet width $W_M$ and magnet thickness $T_M$. Suitable materials for the magnets 110 include, but are not limited to, neodymium-boron-iron and samarium-cobalt.

As illustrated in FIGS. 10 and 13, the exemplary magnet frame 108 includes a disk 116 and a plurality of magnet receptacles 118 that extend completely through the disk and define walls 119 that are located between adjacent magnets 110. Two of the otherwise identical magnet receptacles 118 are relatively long and two are relatively short. The magnet receptacles 118, which are rectangular in shape, have receptacle lengths $L_R$ that are substantially equal to (i.e., about 50-100 μm greater than) the magnet lengths LM, and receptacle widths $W_R$ that are substantially equal to (i.e., about 25-50 μm greater than) the magnet widths $W_M$. The receptacle thicknesses $T_R$, one the other hand, are substantially greater than (i.e., about 100-200 μm greater than) the magnet thicknesses $T_M$. The use of a magnet receptacle that is thicker than the magnet reduces the likelihood of magnet damage, as is discussed in greater detail below with reference to FIG. 14. In those instances where the apparatus includes magnets with circular cross-sections, similar magnet protection functionality can be achieved by employing a frame that is thicker than the magnet diameter. Suitable materials for the frame 108 (as well as the frames 108b-108e described below with reference to FIGS. 21-45), which may be formed by machining or injection molding, include paramagnetic metals, polymers and plastics such as those discussed above in the context of the case 102.

As illustrated for example in FIG. 14, absent a dominant MRI magnetic field B, the magnets 110 will remain aligned with one another in the N-S direction and the N-S orientation of the magnets will be perpendicular to the central axis A1 of the case 102. So oriented, the flat surfaces 114 of the magnets 110 will be aligned with one another, will be perpendicular to the central axis A1 and will face the inner surface 120 of the case 102. The N-S orientation of the magnets 110 remains the same, i.e. perpendicular to the central axis A1, both when the external diametrically magnetized disk-shaped positioning magnet 410 is present (FIG. 9) and when it is not (FIG. 14).

A gap G, resulting from the difference in receptacle thicknesses $T_R$ and magnet thicknesses $T_M$, is located between one of the flat surfaces 114 of each magnet and the inner surface 120 of the case 102 that the flat surface faces. The gap G protects the magnets 110, especially those formed from somewhat brittle ceramic materials, from impacts to the exterior surface of case 102. For example, when the magnet apparatus 100 is oriented in the manner illustrated in FIG. 14 and is impacted by a force F1, the deflection of the case 102 (if any) into the magnet receptacle 118 will not be large enough for the inner surface 120 to impact the adjacent magnet surface 114. If, on the other hand, a force F2 causes deflection of a portion of the case 102 into the magnet receptacle 118, the magnet 110 will slide into the gap G. In both instances, impact on the magnets 100 is minimized. Turning to FIG. 14A, it should be noted that the magnets 110 need not be posited such that one of the flat surfaces 114 is in contact with an inner surface 120 of case 102 to benefit from the gap G. Here, due to the position of the magnet 110, both of the flat surfaces 114 are located adjacent to a portion of the now-split gap G shown in FIG. 14. Accordingly, in those instances where deflection of the case 102 due to force F3 is sufficient to cause the inner surface 120 to come into contact with the adjacent flat surface 114, the magnet 110 can move into the portion of the gap adjacent to the opposite flat surface 114 to prevent magnet damage.

Turning to FIG. 15, when exposed to a dominant MRI magnetic field B, the torque T on the magnets 110 will rotate the magnets about their axis A2 (FIG. 8), thereby aligning the magnetic fields of the magnets 110 with the MRI magnetic field B. The magnet frame 108 will also rotate about axis A1 as necessary to align the magnetic fields of the magnets 110 with the MRI magnetic field B. When the magnet apparatus 100 is removed from the MRI magnetic field B, the magnetic attraction between the magnets 110 will cause the magnets to rotate about axis A2 back to the orientation illustrated in FIG. 14, where they are aligned with one another in the N-S direction and the N-S orientation of the magnets is perpendicular to the central axis A1 of the case 102.

Figure 16:
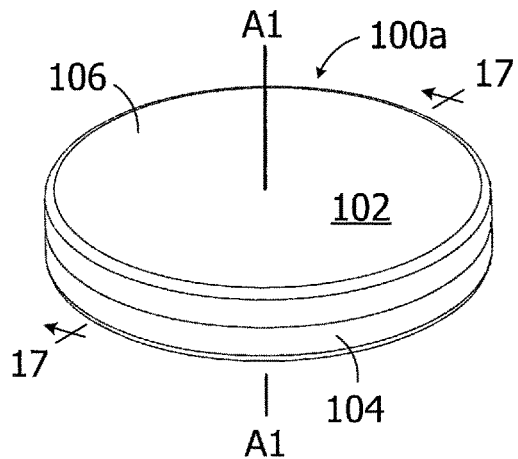
FIG. 16 is a perspective view of an implant magnet apparatus in accordance with one embodiment of a present invention.
Figure 17:
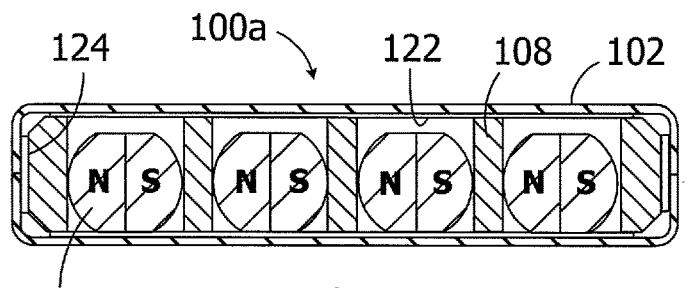
FIG. 17 is a section view taken along line 17-17 in FIG. 16.
Figure 18:
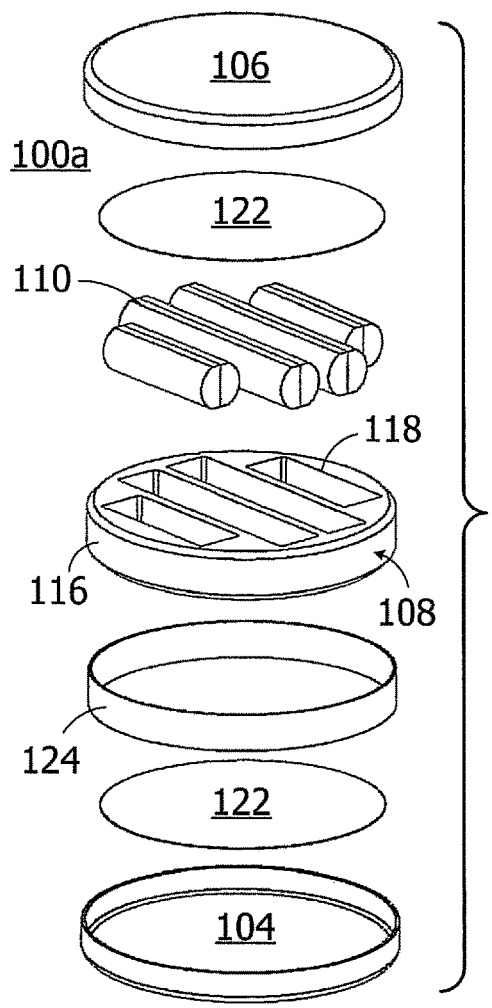
FIG. 18 is an exploded view of the implant magnet apparatus illustrated in FIG. 16.
Figure 18A:
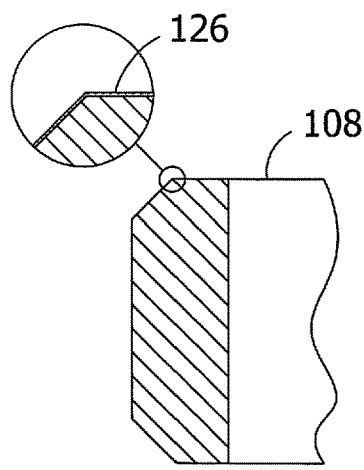
FIG. 18A is an enlarged portion of the section view illustrated in FIG. 17.
Figure 18B:
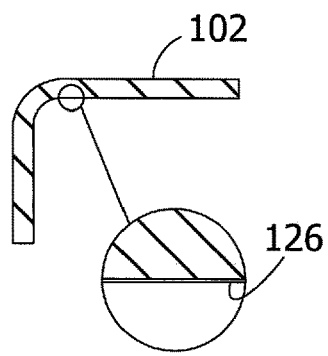
FIG. 18B is an enlarged portion of the section view illustrated in FIG. 17.

To facilitate rotation of the magnet frame 108 and/or the magnets 110, lubricious friction reducing material may be provided between the case 102 and the magnet frame 108 and/or between the magnets 110 and the case 102 and magnet frame 108. For example, the magnet apparatus 100a illustrated in FIGS. 16-18 is substantially similar to the magnet apparatus 100 and similar elements are represented by similar reference numerals. Here, however, a pair of lubricious disks 122 and a lubricious ring 124 formed from PTFE, a hard material (e.g. titanium) with a lubricious coating, or other suitable materials are positioned between the case 102 and the magnet frame 108. Alternatively, instead of two lubricious disks, a single lubricious disk 122 may be positioned on the magnet frame 108 and the portion of the case 102 that will face the external headpiece. In other implementations, a lubricious layer 126 may be added to the inner surface of the case 102 and/or some or all of the various surfaces of the frame 108. The lubricious layer 126 may be in the form of a specific finish of the inner surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. The DLC coating, for example, may be only 0.5 to 5 microns thick. In those instances where the base 104 and a cover 106 are formed by stamping, the finishing process may occur prior to stamping. Micro-balls, biocompatible oils and lubricating powders may also be added to the interior of the case 102 to reduce friction.

Figure 19:
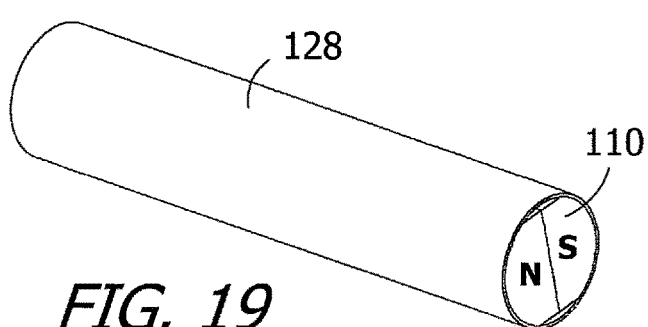
FIG. 19 is a perspective view of a portion of an implant magnet apparatus.
Figure 20:
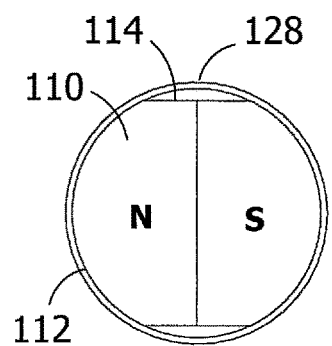
FIG. 20 is an end view of the portion of an implant magnet apparatus illustrated in FIG. 19.
Figure 21:
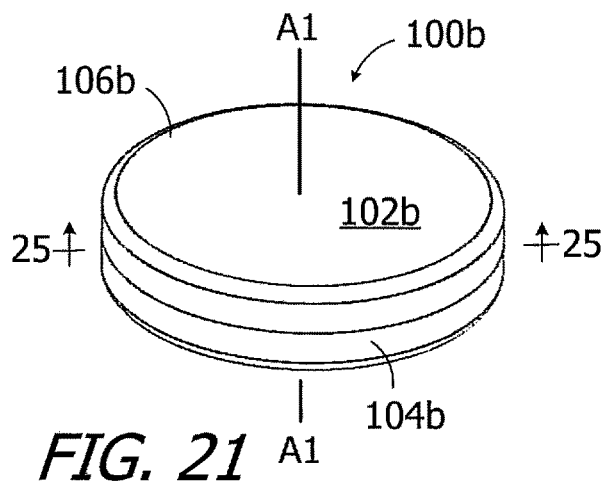
FIG. 21 is a perspective view of an implant magnet apparatus in accordance with one embodiment of a present invention.
Figure 22:
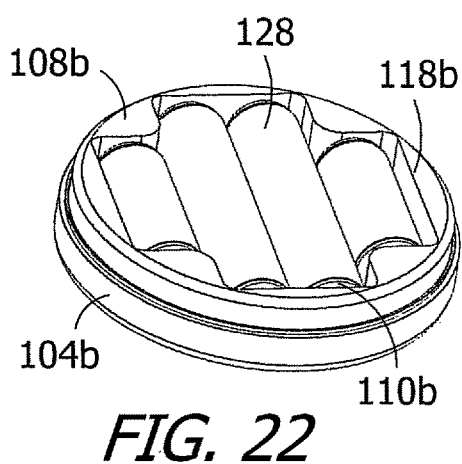
FIG. 22 is a perspective view of a portion of the implant magnet apparatus illustrated in FIG. 21.
Figure 23:
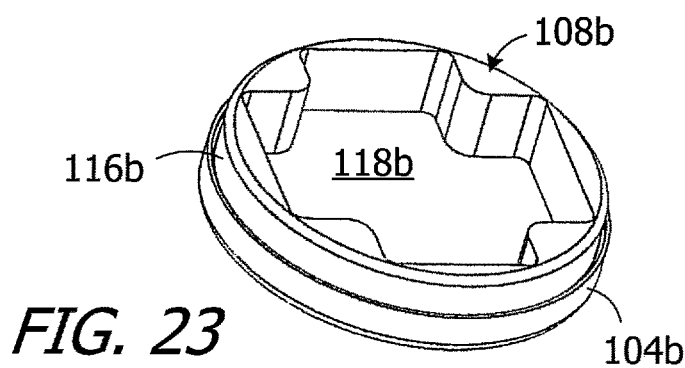
FIG. 23 is a perspective view of a portion of the implant magnet apparatus illustrated in FIG. 21.
Figure 24:
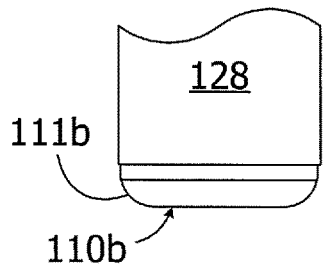
FIG. 24 is a plan view of a portion of the implant magnet apparatus illustrated in FIG. 21.

Alternatively, or in addition, the magnets 110 may be located within tubes 128 formed from low friction material, as is illustrated in FIGS. 19 and 20. Suitable materials for the tube 128 include polymers, such as silicone, PEEK and other plastics, PTFE, and PEEK-PTFE blends, and paramagnet metals. The magnets 110 may be secured to the tubes 128 such that the each tube rotates with the associated magnet about its axis A2, or the magnets may be free to rotate relative to the tubes. The magnet/tube combination is also more mechanically robust than a magnet alone. The magnets 110 may, in place of the tube 128, be coated with the lubricious materials discussed above.

Another exemplary magnet apparatus, which is generally represented by reference numeral 100b in FIGS. 21-25, is substantially similar to the magnet apparatus 100 and similar elements are represented by similar reference numerals. To that end, the magnet apparatus 100b includes a case 102b, with a base 104b and a cover 106b, a magnet frame 108b, and a plurality of elongate diametrically magnetized magnets 110b within the frame. The frame 108b does not include a plurality of magnet receptacles and walls 119 (FIGS. 10 and 13) that separate adjacent magnets, as does the frame 108, or any other frame structures that separate the magnets. Instead, the frame 108b includes a disk 116b and a single magnet receptacle 118b that extends completely through the disk. The magnet receptacle 118b is configured to hold all of the magnets 110b (four in the illustrated embodiment) and includes a relatively long portion and two relatively short portions. The magnets 110b are elongate diametrically magnetized magnets that are circular in cross-section, located within low friction tubes 128, and include rounded corners 111b. The magnets 110 with flat surface 114 (described above with reference to FIGS. 19 and 20) may also be employed.

Figure 25:
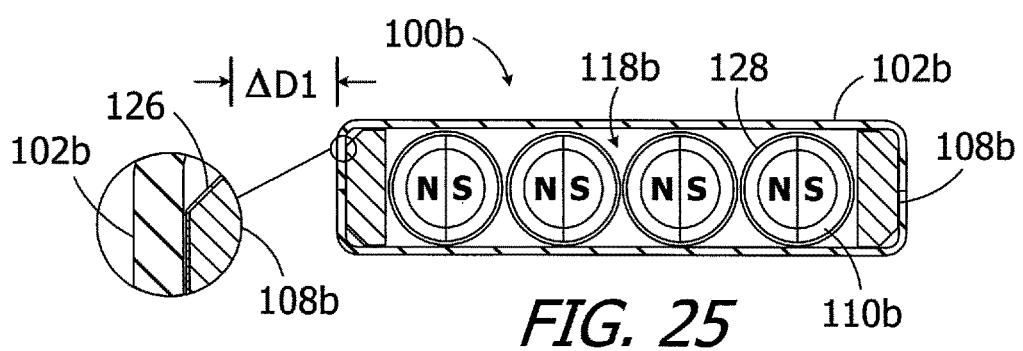
FIG. 25 is a section view taken along line 25-25 in FIG. 21.
Figure 26:
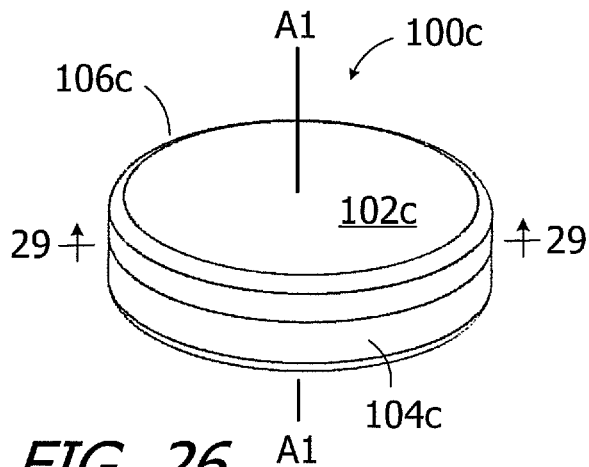
FIG. 26 is a perspective view of an implant magnet apparatus in accordance with one embodiment of a present invention.
Figure 27:
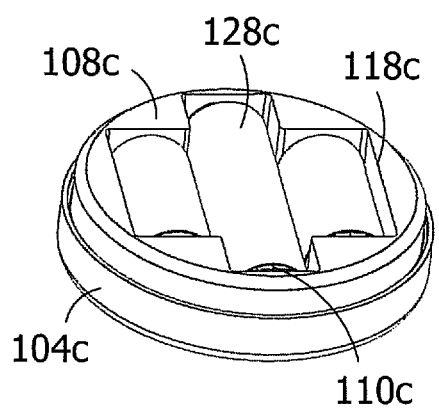
FIG. 27 is a perspective view of a portion of the implant magnet apparatus illustrated in FIG. 26.
Figure 28:
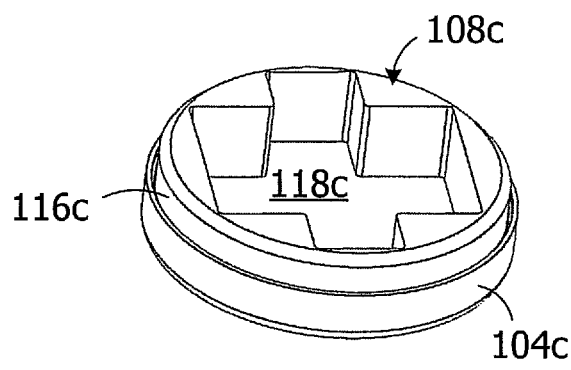
FIG. 28 is a perspective view of a portion of the implant magnet apparatus illustrated in FIG. 26.

In the illustrated implementation, the surfaces of the frame 108b are coated with a lubricious layer 126 (e.g., DLC), while the inner surfaces of the case 102 do not include a lubricious layer. The very thin lubricious layer 126 reduces friction between the case 102 and frame 108b, while the low friction tubes 128 reduce friction between adjacent magnets 110b as well as between the case 102 and the magnets 110b. As such, the aforementioned lubricious disks 122 and a lubricious ring 124 may be omitted, thereby reducing the diameter and thickness of the magnet apparatus 100b as compared to magnet apparatus 100a (FIGS. 16-18). Additionally, although the diameters of the magnets 110b in the exemplary magnet apparatus 100b are equal to the widths of the magnets 110 (FIG. 11) in the exemplary magnet apparatus 100, the omission of the walls 119 between the magnets reduces the overall diameter of the magnet apparatus 100b by an amount $\Delta D1$ (FIG. 25). The diameter of the case 102b is 12.6 mm, and the thickness is 2.9 mm, in the illustrated embodiment.

The overall diameter of the magnet apparatus may be further reduced by reducing the number of magnets in the apparatus while maintaining the same magnetic strength by including the same total volume of magnet material. To that end, and referring to FIGS. 26-29, the exemplary magnet apparatus 100c is substantially similar to magnet apparatus 100b and similar elements are represented by similar reference numbers. The magnet apparatus 100c includes a case 102c, with a base 104c and a cover 106c, a magnet frame 108c, and a plurality of elongate diametrically magnetized magnets 110c within the frame. The frame 108c includes a disk 116c and a single magnet receptacle 118c, with a relatively long portion and two relatively short portions, which extends completely through the disk.

Figure 29:
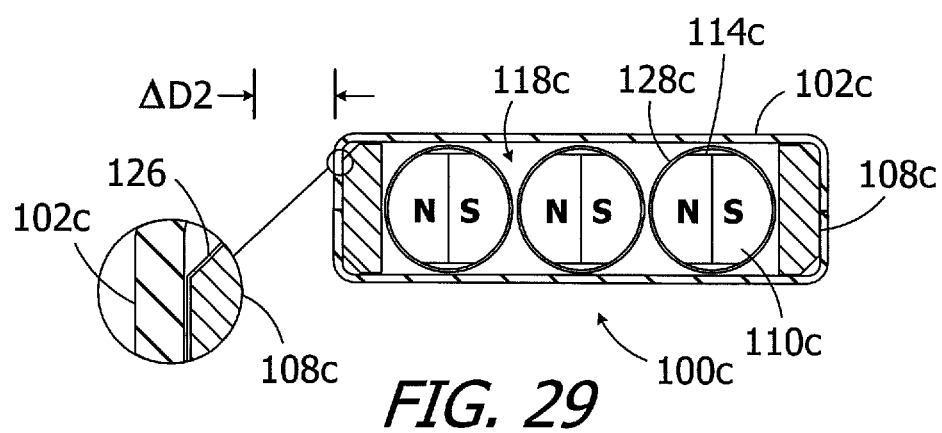
FIG. 29 is a section view taken along line 29-29 in FIG. 26.
Figure 30:
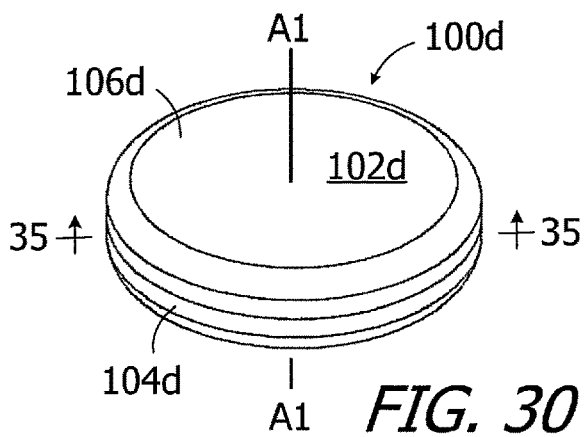
FIG. 30 is a perspective view of an implant magnet apparatus in accordance with one embodiment of a present invention.
Figure 31:
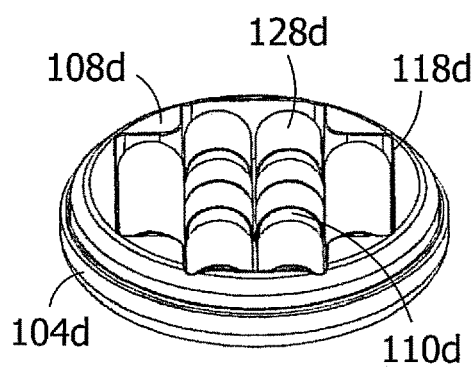
FIG. 31 is a perspective view of a portion of the implant magnet apparatus illustrated in FIG. 30.
Figure 32:
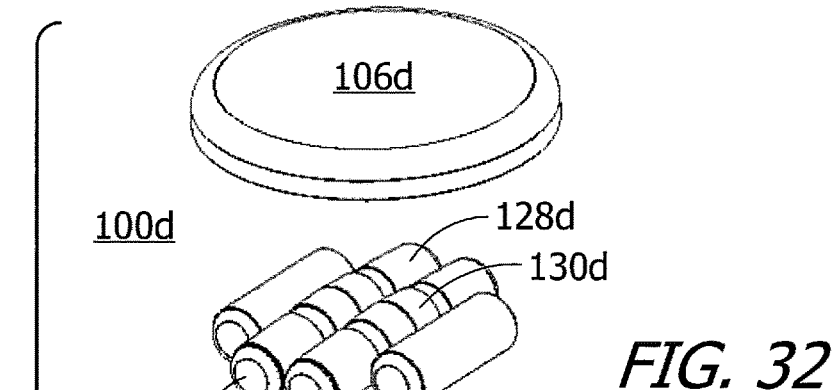
FIG. 32 is an exploded view of the implant magnet apparatus illustrated in FIG. 30.
Figure 33:
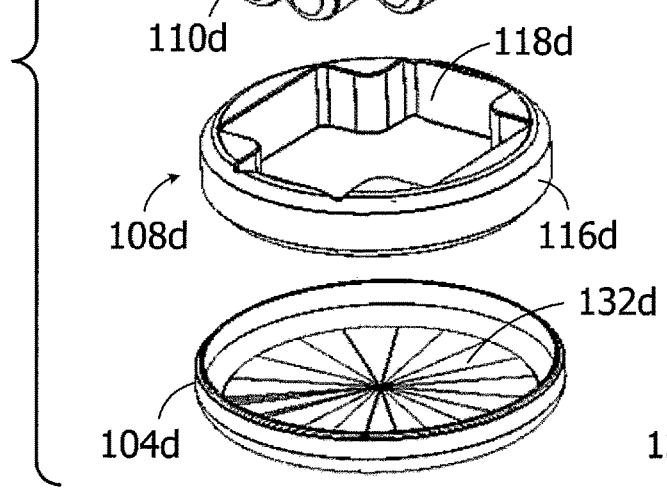
FIG. 33 is an end view of a portion of the implant magnet apparatus illustrated in FIG. 30.
Figure 34:
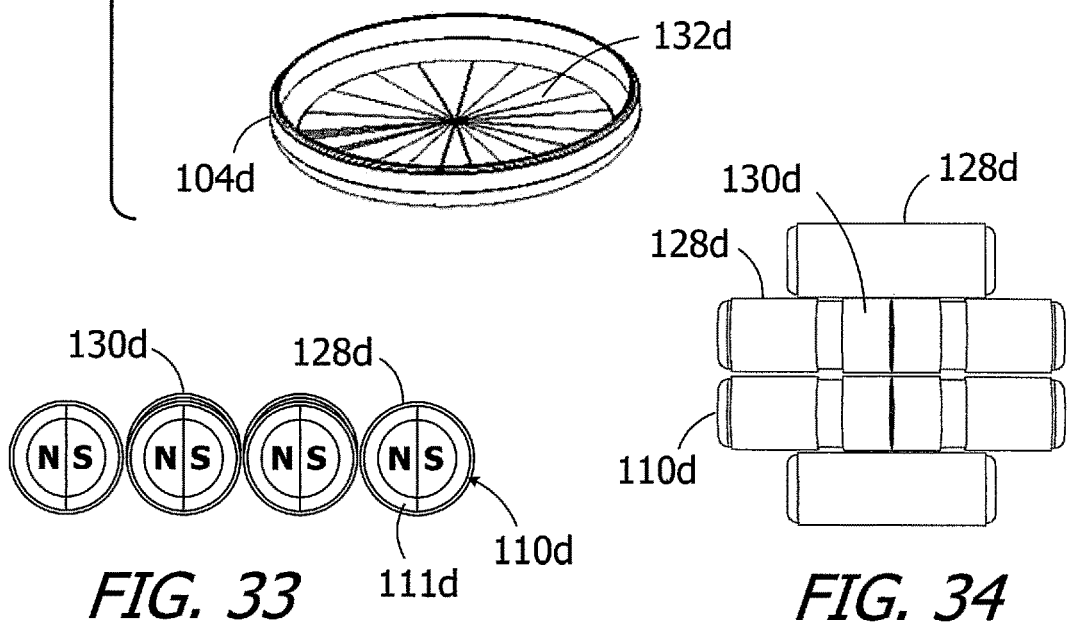
FIG. 34 is a top view of a portion of the implant magnet apparatus illustrated in FIG. 30.

Here, three magnets 110c with flat portions 114c are located within the magnet receptacle 118c. Low friction tubes 128c cover the magnets 110c. The reduction in the number of magnets reduces the overall diameter of the magnet apparatus 100c, as compared to the magnet apparatus 100b, by an amount $\Delta D2$ (FIG. 29). It should be noted that the widths of the magnets 110c (FIG. 29) are greater than diameters of the magnets 110b (FIG. 25) in order to provide the same volume of magnetic material, which results in a slight increase in the overall thickness of the magnet apparatus 100c as compared to the magnet apparatus 100b. The diameter of the case 102c is 11.6 mm, and the thickness is 3.2 mm, in the illustrated embodiment.

Another exemplary magnet apparatus, which is generally represented by reference numeral 100d, is illustrated in FIGS. 30-41. Magnet apparatus 100d is substantially similar to the magnet apparatus 100b and similar elements are represented by similar reference numerals. To that end, the magnet apparatus 100d includes a case 102d, with a base 104d and a cover 106d, a magnet frame 108d, and a plurality of elongate diametrically magnetized magnets 110d within the frame. The frame 108d includes a disk 116d and a single magnet receptacle 118d that extends completely through the disk. The magnet receptacle 118d is configured to hold all of the magnets 110d (six in the illustrated embodiment) and includes a relatively long portion and two relatively short portions. The magnets 110d are elongate diametrically magnetized magnets that are circular in cross-section, located within low friction tubes 128d, and include rounded corners 111d. The magnets 110 with flat surface 114 (described above with reference to FIGS. 19 and 20) may also be employed.

Here, however, at least two of the magnets are slightly non-perpendicular to the central axis A1 (i.e., have axes that are offset from perpendicular by any and all angles up to and including 5 degrees), as is discussed in greater detail below with reference to FIGS. 35-37. Referring first to FIGS. 30-34, four of the magnets 110d in the illustrated implementation have a longitudinal axis (or "axis") that is slightly non-perpendicular to the central axis A1 (referred to herein as "slightly non-perpendicular magnets") and the remaining two magnets have respective axes that are perpendicular to the central axis A1 (referred to herein as the "perpendicular magnets"). The slightly non-perpendicular magnets are arranged in two pairs, the magnets in each pair are positioned end-to-end, and the ends of the magnets in each pair abut one another near the central axis A1.

The north dipoles of the slightly non-perpendicular magnets 110d in the exemplary magnet apparatus 100d are aligned with one another within each pair, as are the south dipoles, so that each pair functions in a manner similar to the longer magnets 110b of the magnet apparatus 100b. Such N-N and S-S dipole alignment can be problematic during assembly because the dipoles repel one another. Connectors 130d, which are discussed below with reference to FIGS. 40 and 41, may be provided to maintain the desired orientation of the magnets 110d in each pair during the assembly process. Although the strength of the connection between the magnets 110d and the connectors 130d is sufficient to facilitate assembly, the magnets will rotate about their longitudinal axis as necessary when exposed to an MRI magnet field. The low friction tubes 128d cover less of the connected magnets 110d due to the presence of the connector 130d. Other apparatus and methods for accommodating dipole alignment during the assembly process are discussed below with reference to FIGS. 42-45.

Turning to FIGS. 35-37, the orientation of the slightly non-perpendicular magnets 110d may be a function of the shape of the case 102. In the illustrated implementation, the case base 104d includes a convex inner surface 132d. The central axis A1 passes through the apex of the convex inner surface 132d, and the abutting ends of the slightly non-perpendicular magnets 110d are adjacent to the apex. The use of the frame 108d and the shape of the convex inner surface 132d results in the axes A3 of the slightly non-perpendicular magnets 110d being slightly non-perpendicular to the central axis A1 (i.e., offset from perpendicular by any non-zero angle Θ up to 5 degrees, and by 3 degrees in the illustrated embodiment) and the axes A2 of the perpendicular magnets 110d being perpendicular to the central axis A1. These magnet orientations are maintained as the frame 108d rotates relative to the case 102d and/or as the magnets rotate about their respective axes A2 and A3.

The magnet frame may be configured to accommodate the curvature of the convex inner surface 132d of the case base 104d. To that end, and referring to FIGS. 38 and 39, the exemplary frame 108d includes a concave bottom surface 134d with a shape corresponding to that of the convex inner surface 132d of the case base 104d. The shape of the frame upper surface 136d may similarly correspond to that of the inner surface 133d of the case cover 106d and, in the illustrated implementation, both surfaces are flat.

Figure 40:
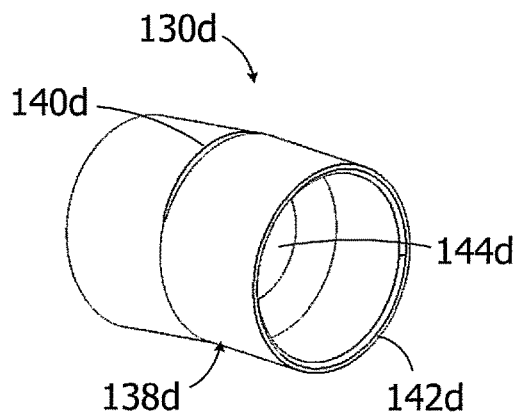
FIG. 40 is a perspective view of a portion of the implant magnet apparatus illustrated in FIG. 30.
Figure 41:
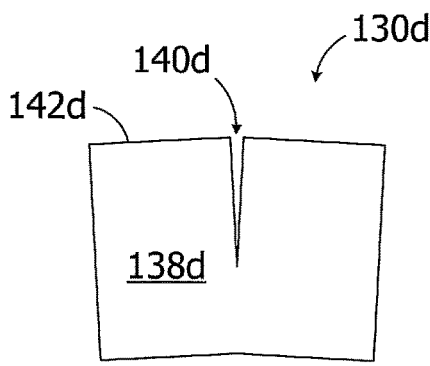
FIG. 41 is a side view of a portion of the implant magnet apparatus illustrated in FIG. 30.

As illustrated for example in FIGS. 40 and 41, the exemplary connectors 130d each include a pair of connector members 138d that are attached to one another at an angle (corresponding to the relative orientation of the associated slightly non-perpendicular magnets 110d) with a gap 140d therebetween. Each connector member 138d includes a tubular wall 142d and an end wall 144d. The respective sizes of the magnets 110d and the tubular walls 142d results in an interference fit that is sufficient to maintain end-to-end dipole alignment during assembly, but will allow the magnets will rotate about their longitudinal axis relative to the associated connector 130d as necessary when exposed to an MRI magnet field. In some instances, adhesive may be used to secure the ends of the magnets 110d to the connectors 130d. The adhesive bonds will fail, thereby permitting magnet rotation, under the torque imparted by an MRI magnet field.

Figure 42:
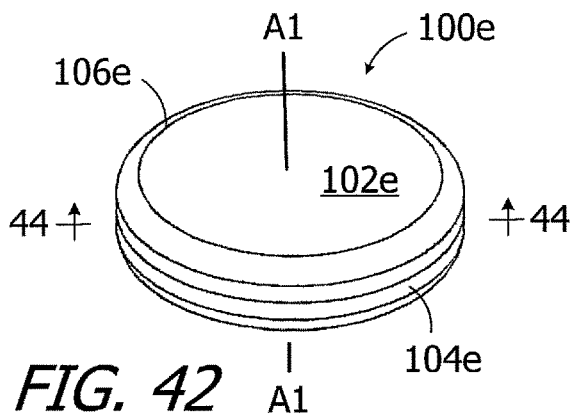
FIG. 42 is a perspective view of an implant magnet apparatus in accordance with one embodiment of a present invention.
Figure 43:
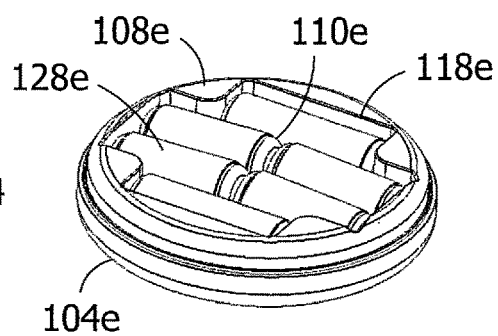
FIG. 43 is a perspective view of a portion of the implant magnet apparatus illustrated in FIG. 42.
Figure 44:
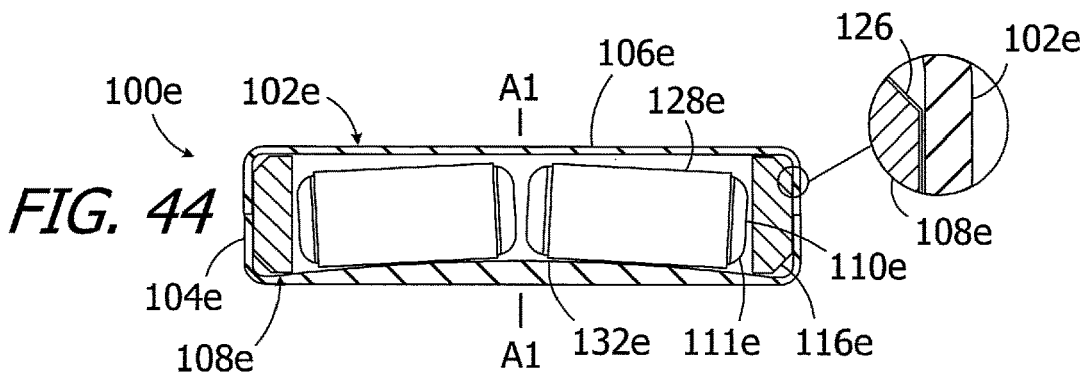
FIG. 44 is a section view taken along line 44-44 in FIG. 42.

Another exemplary magnet apparatus, which is generally represented by reference numeral 100e, is illustrated in FIGS. 42-44. Magnet apparatus 100e is substantially similar to the magnet apparatus 100d and similar elements are represented by similar reference numerals. To that end, the magnet apparatus 100e includes a case 102e, with a base 104e and a cover 106e, a magnet frame 108e, and a plurality of elongate diametrically magnetized magnets 110e within the frame. In the illustrated implementation, the case base 104e includes a convex inner surface 132e. The frame 108e includes a disk 116e and a single magnet receptacle 118e that extends completely through the disk. The magnet receptacle 118e is configured to hold all of the magnets 110e (six in the illustrated embodiment) and includes a relatively long portion and two relatively short portions. The magnets 110e are elongate diametrically magnetized magnets that are circular in cross-section, located within low friction tubes 128e, and include rounded corners 111e. The magnets 110 with flat surface 114 (described above with reference to FIGS. 19 and 20) may also be employed.

Here, however, the above-described connector 130d has been omitted, and there is no other instrumentally connecting the end of the slightly non-perpendicular magnets 110e to one another. In some instances, the magnets 110e may be de-magnetized (or "non-magnetic") during the assembly process and then magnetized after the magnet apparatus 100e has been assembled. It should also be noted here that the magnets in any of the other embodiments described herein may be magnetized either before or after assembly.

Figure 45:
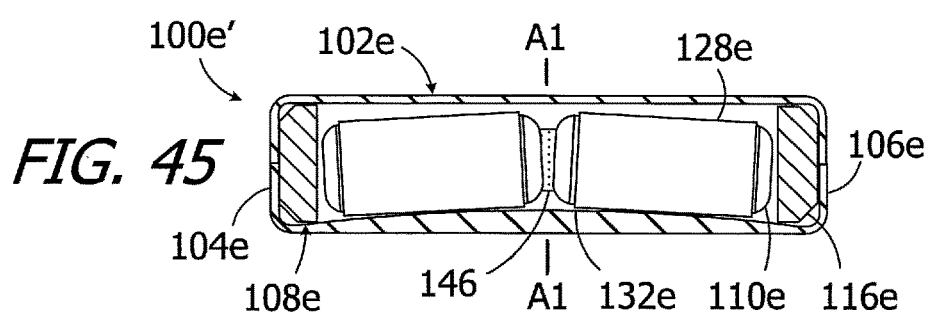
FIG. 45 is a section view of an implant magnet apparatus in accordance with one embodiment of a present invention.

Turning to FIG. 45, the exemplary magnet apparatus 100e' is essentially identical to the magnet apparatus 100e and similar elements are represented by similar reference numerals. Here, however, the ends of the slightly non-perpendicular magnets 110e are secured to one other with adhesive 146. The bond formed by the adhesive 146 will maintain end-to-end dipole alignment during assembly, but will fail and allow the magnets 110e to rotate about their respective longitudinal axes when exposed to an MRI magnet field.

Figure 46:
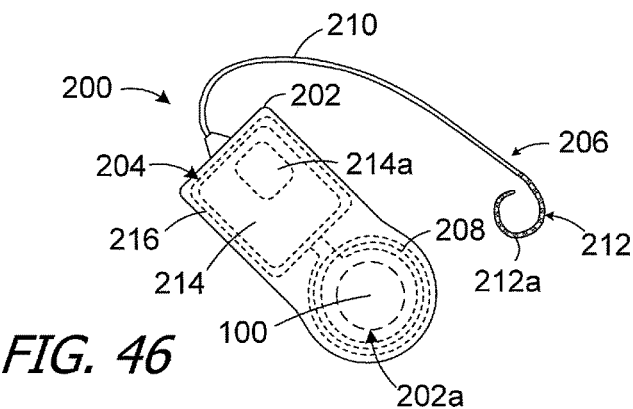
FIG. 46 is a plan view of a cochlear implant in accordance with one embodiment of a present invention.

One example of a cochlear implant (or "implantable cochlear stimulator") including the present magnet apparatus 100 (or 100a-100e') is the cochlear implant 200 illustrated in FIG. 46. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 212a (e.g., platinum electrodes) in the array 212 to the other end of the flexible body. The magnet apparatus 100 is located within a region encircled by the antenna 208 (e.g., within an internal pocket 202a defined by the housing 202) and insures that an external antenna (discussed below) will be properly positioned relative to the antenna 208. The exemplary processor assembly 204, which is connected to the electrode array 212 and antenna 208, includes a printed circuit board 214 with a stimulation processor 214a that is located within a hermetically sealed case 216. The stimulation processor 214a converts the stimulation data into stimulation signals that stimulate the electrodes 212a of the electrode array 212.

Figure 47:
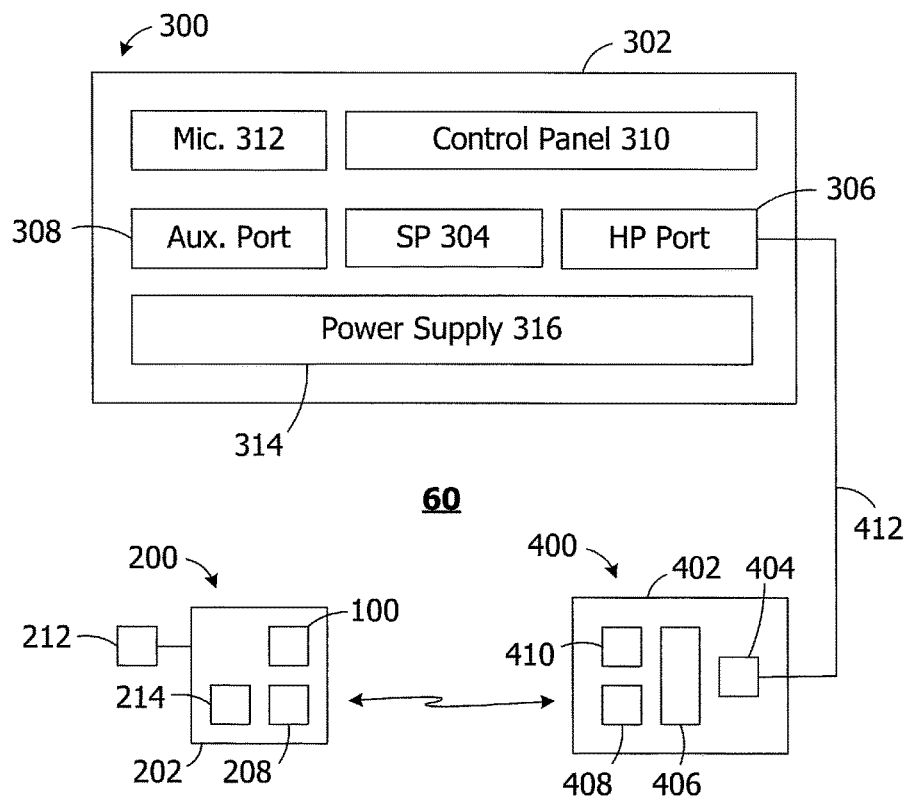
FIG. 47 is a block diagram of a cochlear implant system in accordance with one embodiment of a present invention.

Turning to FIG. 47, the exemplary cochlear implant system 60 includes the cochlear implant 200, a sound processor, such as the illustrated body worn sound processor 300 or a behind-the-ear sound processor, and a headpiece 400.

The exemplary body worn sound processor 300 in the exemplary ICS system 60 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and a diametrically magnetized disk-shaped positioning magnet 410, that are carried by the housing. The headpiece 400 may be connected to the sound processor headpiece port 306 by a cable 412. The positioning magnet 410 is attracted to the magnet apparatus 100 of the cochlear stimulator 200, thereby aligning the antenna 408 with the antenna 208. The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 214a converts the stimulation data into stimulation signals that stimulate the electrodes 212a of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances. The functionality of the sound processor 300 and headpiece 400 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A magnet apparatus, comprising:
a case defining a central axis;
a magnet frame within the case and rotatable relative to the case about the central axis of the case; and
a plurality of elongate diametrically magnetized magnets that are located in the magnet frame, the magnets each defining a longitudinal axis and a N-S direction and being rotatable about its respective longitudinal axis relative to the magnet frame and configured to align with one another in the N-S direction in the absence of an external magnetic field.

2. A magnet apparatus as claimed in claim 1, wherein
the magnets each define a N-S rotational orientation; and
the magnets are magnetically attracted to one another in a manner that, absent the presence of a dominant magnetic field, the N-S rotational orientation of the magnets is perpendicular to the central axis of the case.

3. A magnet apparatus as claimed in claim 1, wherein
the magnets each define a length in the direction of the longitudinal axis, a thickness, and a width; and
the length is greater than the width and the thickness.

4. A magnet apparatus as claimed in claim 3, wherein
the width is greater than the thickness.

5. A magnet apparatus as claimed in claim 4, wherein
the width extends in the N-S direction.

6. A magnet apparatus as claimed in claim 3, wherein
the magnets each define a cross-section, including first and second curved surfaces that are connected to one another by first and second flat surfaces, in a plane perpendicular to the longitudinal axis;
the curved surfaces are separated from one another in the N-S direction; and
the flat surfaces are separated from one another in a direction perpendicular to the N-S direction.

7. A magnet apparatus as claimed in claim 3, wherein
the magnet frame defines a thickness; and
the thickness of the magnets is less than the thickness of the magnet frame.

8. A magnet apparatus as claimed in claim 7, wherein
the magnet frame includes a plurality of magnet recesses, defining recess lengths and recess widths, in which the plurality of magnets are located;
the magnet recess lengths are substantially equal to the magnet lengths; and
the magnet recess widths are substantially equal to the magnet widths.

9. A magnet apparatus as claimed in claim 3, wherein
at least one of the magnets is longer than an adjacent magnet.

10. A magnet apparatus as claimed in claim 1, wherein
the magnets each define a non-circular cross-section in a plane perpendicular to the longitudinal axis.

11. A magnet apparatus as claimed in claim 1, wherein
the longitudinal axes of the magnets are parallel to one another.

12. A magnet apparatus as claimed in claim 1, further comprising:
lubricious material between the case and the magnet frame.

13. A magnet apparatus as claimed in claim 1, further comprising:
lubricious material between the magnets and the magnet frame.

14. A magnet apparatus as claimed in claim 1, wherein
the magnets are located within respective tubes formed from lubricious material.

15. A magnet apparatus in claim 1, wherein
the magnet frame includes a single magnet recess in which all of the plurality of magnets are located with no portion of the magnet frame located between adjacent magnets.

16. A magnet apparatus as claimed in claim 15, wherein the single magnet recess includes a first portion and second and third portions that are shorter than the first portion.

17. A magnet apparatus as claimed in claim 1, wherein the magnet frame includes a lubricious outer layer.

18. A magnet apparatus as claimed in claim 17, wherein the case defines an inner surface that does not include a lubricious layer.

19. A magnet apparatus as claimed in claim 17, wherein the magnets define respective outer surfaces; and
at least a portion of the outer surfaces of the magnets is covered by lubricious material.

20. A magnet apparatus as claimed in claim 1, wherein the longitudinal axes of the magnets are at least substantially perpendicular to the central axis.

21. A magnet apparatus, comprising:
a case defining a central axis;
a magnet frame within the case and rotatable about the central axis of the case;
a plurality of elongate diametrically magnetized perpendicular magnets that are located in the magnet frame, the perpendicular magnets each defining a longitudinal axis that is perpendicular to the central axis, a respective N-S direction that is perpendicular to the longitudinal axis and a respective N-S rotational orientation, being rotatable about its respective longitudinal axis relative to the magnet frame, and configured to align with one another in the N-S direction in the absence of an external magnetic field;
a plurality of elongate diametrically magnetized non-perpendicular magnets that are located in the magnet frame, the non-perpendicular magnets each defining a longitudinal axis that is not perpendicular to the central axis, a respective N-S direction that is perpendicular to the longitudinal axis and a respective N-S rotational orientation, being rotatable about its respective longitudinal axis relative to the magnet frame, and configured to align with one another in the N-S direction in the absence of an external magnetic field;
the perpendicular magnets and non-perpendicular magnets being configured to be magnetically attracted to one another in a manner that, absent the presence of a dominant magnetic field, the N-S rotational orientation of the perpendicular magnets and non-perpendicular magnets is perpendicular to the central axis of the case.

22. A magnet apparatus as claimed in claim 21, wherein two non-perpendicular magnets include longitudinal ends and are positioned end-to-end with adjacent ends near the central axis; and
the adjacent ends are connected to one another with a connector that is configured to prevent rotation of the two non-perpendicular magnets about their respective longitudinal axes relative to the connector in the absence of an MRI magnetic field and to permit rotation of the two non-perpendicular magnets about their respective longitudinal axes relative to the connector in the presence of an MRI magnetic field.

23. A magnet apparatus as claimed in claim 21, wherein the longitudinal axis of one or more of the non-perpendicular magnets is offset from perpendicular to the central axis by 5 degrees or less.

* * * * *